US00PP15868P2

(12) United States Plant Patent
Toyama

(10) Patent No.: US PP15,868 P2
(45) Date of Patent: Jul. 19, 2005

(54) CHERRY TREE 'PC8011-3'

(50) Latin Name: *Prunus avium*
Varietal Denomination: PC8011-3

(75) Inventor: Thomas Toyama, Eugene, OR (US)

(73) Assignee: Washington State University Research Foundation, Pullman, WA (US)

( * ) Notice: Subject to any disclaimer, the term of this patent is extended or adjusted under 35 U.S.C. 154(b) by 25 days.

(21) Appl. No.: 10/642,090

(22) Filed: Aug. 14, 2003

Related U.S. Application Data

(60) Provisional application No. 60/404,078, filed on Aug. 15, 2002.

(51) Int. Cl.[7] ..... A01H 5/00
(52) U.S. Cl. ..... Plt./181
(58) Field of Search ..... Plt./181

*Primary Examiner*—Kent Bell
(74) *Attorney, Agent, or Firm*—Stratton Ballew PLLC

(57) ABSTRACT

A new cultivar of sweet cherry tree named 'PC-8011-3' is disclosed. The new cultivar is notable for its large, firm attractive blushed yellow fruit of excellent quality and flavor.

1 Drawing Sheet

Latin name of the genus and species of the plant claimed: *Prunus avium.*

Variety denomination: 'PC8011-3'.

BRIEF DESCRIPTION OF THE PHOTOGRAPHS

The photograph shows the fruit of the new cultivar.

DETAILED BOTANICAL DESCRIPTION OF THE VARIETY

The present invention relates to a new variety of sweet cherry tree which bears large, firm attractive fruits of excellent quality and flavor. 'PC8011-3' was developed at the Washington State University Irrigated Agriculture Research and Extension Center (I.A.R.E.C.) at Prosser, Wash. It was selected from among several seedlings that resulted from a controlled cross 'PC7147-4' (seed parent, unpatented variety) and 'PC66138-2' (pollen parent, unpatented variety) made in 1980, and has continued to be tested as 'PC8011-3'. Second test trees were planted on the Roza Unit of the center in the spring of 1990.

Fruit of 'PC8011-3' is large, yellow with red blush, similar to 'Rainier,' of excellent quality, with superior flavor. 'PC8011-3' ripens earlier than 'Rainier.'

'PC8011-3' is distinguishable from its parents 'PC7147-4' and 'PC66138-2' by its yellow ground color. Both parent varieties are dark skinned cherries.

'PC8011-3' is self-sterile so pollenizer trees are needed. Trees are spindly. All second and third generation test trees observed closely have shown no tendency toward the 'cherry crinkle-leaf' genetic disorder which is common in 'Bing,' (unpatented variety) as well as in several other varieties of sweet cherry.

Asexual reproduction of this new and distinct cultivar at our test facilities near Prosser shows that its desirable characteristics come true to form and are established and transmitted through succeeding propagations by grafting.

The following is a detailed botanical description of 'PC8011-3,' a new and distinct cultivar of *Prunus avium.*, based on observations of 21 to 23 year old trees made during the 2002, 2003 and 2004 growing seasons in Prosser, Wash. All colors are described according to The Royal Horticultural Society Color Chart. It should be understood that the botanical and analytical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:

*Size.*—Large; size of a 22 year old tree is 14 feet high and 20 feet wide.

*Vigor.*—Vigorous; growth of 22 year old tree is 18 inches per year.

*Branching habit.*—Upright-spreading.

*Density.*—Forms many spurs.

*Form.*—Round-headed when mature.

*Hardiness.*—Hardy in area where tested (lower Yakima Valley of Washington); USDA hardiness zone 5b.

*Production.*—Less productive than 'Rainier'.

*Bearing.*—Consistent, regular.

*Trunk.*—Size: Stocky, diameter 41 cm at 20 cm above soil level. Bark texture: Typical for sweet cherry. Bark color: Gray-brown 177A. Lenticels: Numerous; large 2–10 mm in diameter; brown.

*Branch.*—Size: Stocky, representative branch at 130 cm above the ground is 14 cm diameter. Crotch angle of bearing branches: 60°–75° from vertical. Texture: Average, typical for sweet cherry. Color: First year wood, light green 144C; second year wood, grey green 197C. Lenticels: Numerous; medium, 1–5 mm in diameter; brown.

*Leaves.*—Measurements are from mature leaves attached at midpoint of actively growing upright shoots of current season's growth. Size: Very large, 15–19 cm long, 5.5–8 cm wide. Form: Lanceolate with acuminate tip, margin dentate. Color: Upper surface glossy green 137A, lower surface light green 137C. Midvein: Large; upper surface green 141C, lower surface green 142C, 2 mm in diameter. Petiole: Medium to long: 3.5 to 4.0 cm long, 2–3 mm thick; red 145B on upper side, green 142C on under side.

Glands: 2–3, large, avg. 1.8 mm long, avg. 1.2 mm wide; color red 46A and 53A, yellow green 150B and 150C; oval.

Flowers:

*Buds.*—5 to 6 per spur, avg. 4.7 mm long; 2.5 mm wide; brown 165A; pedicel length 2–5 cm.

*Bloom time.*—First bloom Apr. 4, 2002; full bloom Apr. 14, 2002 in Prosser, Wash.

Fruit:

*Maturity.*—Eating ripe June 24 at Prosser test site (9 year average).

*Date of first picking.*—June 13 at Prosser.

*Date of last picking.*—July 16 at Prosser.

*Size.*—Large, 9–12 g; diameter transversely across suture 2.5–2.6 cm; diameter apically 2.3–2.4 cm.

*Form.*—Reniform, uniform, symmetrical.

*Suture.*—Very shallow.

*Stem.*—Medium, thin, 1.1 mm, 3–3.5 cm in length; light green 143C.

*Cavity.*—Shallow, flattened at pedicel, rounding toward shoulders; diameter 11.6 mm shoulder to shoulder, depth 2.4 mm.

*Skin.*—Thickness: medium. Texture: Medium. Tenacity: Tenacious to flesh. Tendency to crack: Susceptible to cracking caused by prolonged rains about the same as 'Rainier'; none in dry season. Down: Wanting. Color: Yellow 3C with pink to red 46A blush.

*Flesh.*—Color yellow 4D. Texture: Firm, crisp, similar to 'Rainier'. Juciness: Average. Eating quality: Superior.

*Stone.*—Type: Semi-free. Size — small, 1 cm long, 1 cm wide. Oval, rounded apex and base. Color brown 158A. Use: Mid season shipping to premium fresh markets. Keeping quality: Good. Resistance to insects and diseases: Susceptible to bacterial canker (pseudomonas), no cherry crinkle-leaf noted. Shipping quality: Firm but will show bruising similar to 'Rainier'.

We claim:

1. A new and distinct cherry tree, substantially as shown and described herein.

* * * * *

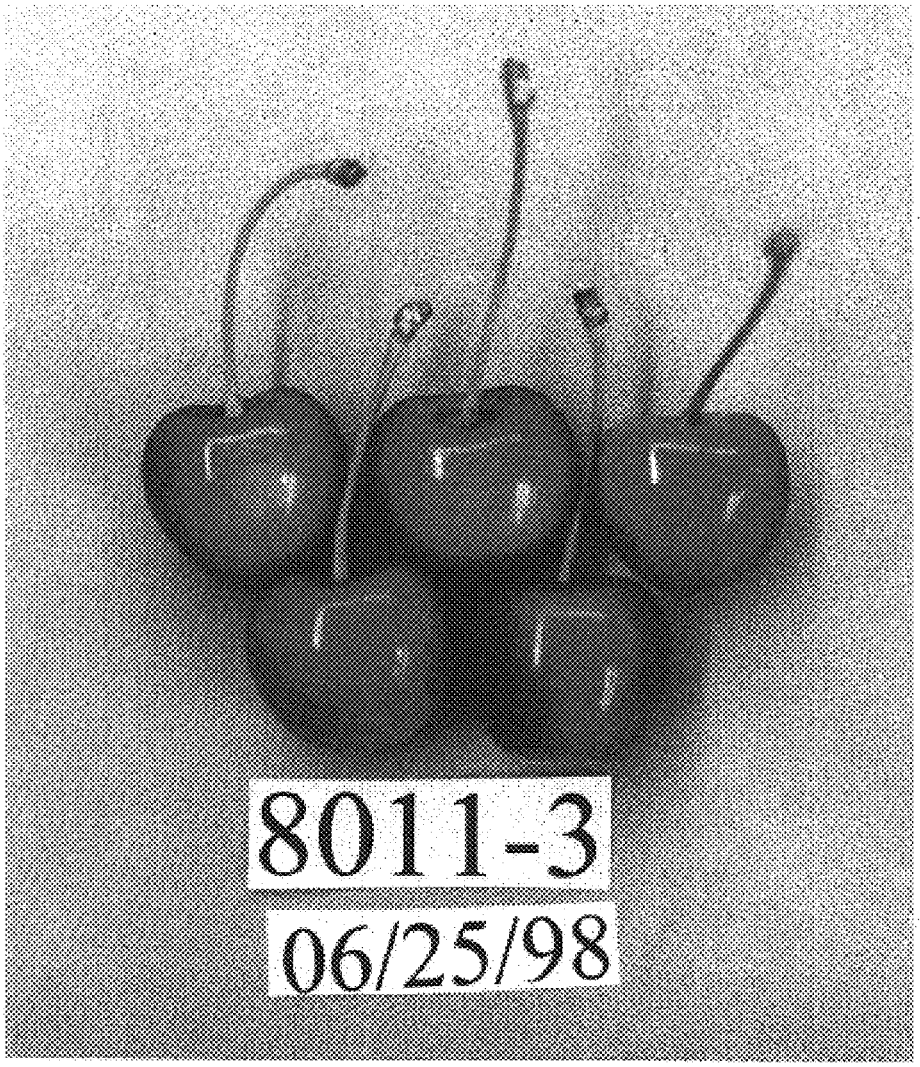
8011-3
06/25/98